United States Patent [19]

Spector

[11] Patent Number: 5,178,839

[45] Date of Patent: Jan. 12, 1993

[54] KIT FOR FORMULATING AND GENERATING DIFFERENT AROMAS

[76] Inventor: Donald Spector, 380 Mountain Rd., Union City, N.J. 07087

[21] Appl. No.: 755,102

[22] Filed: Sep. 5, 1991

[51] Int. Cl.⁵ .......................... A61L 9/00; A61L 9/02; A61L 9/03
[52] U.S. Cl. ...................................... 422/123; 422/4; 422/5; 422/21; 422/120; 422/125; 422/306; 422/307; 219/10.55 E; 206/472; 434/377
[58] Field of Search ................... 422/120, 123, 125, 4, 422/5, 21, 306, 307; 219/10.55 E; 206/472; 434/377

[56] References Cited

U.S. PATENT DOCUMENTS

| | | | |
|---|---|---|---|
| 1,403,548 | 1/1922 | Gudeman | 422/125 |
| 1,546,302 | 7/1925 | Mehigan | 434/377 |
| 2,874,707 | 2/1959 | Koppel | 206/472 X |
| 3,191,319 | 6/1965 | Waisgerber | 206/472 X |
| 4,002,355 | 1/1977 | Sendor | 206/472 X |
| 4,556,539 | 12/1985 | Spector | 422/125 |
| 4,629,604 | 12/1986 | Spector | 422/125 X |
| 4,695,434 | 9/1987 | Spector | 422/125 X |
| 4,745,248 | 5/1988 | Hayes | 219/10.55 E X |
| 4,797,521 | 1/1989 | Liwski | 219/10.55 F X |

FOREIGN PATENT DOCUMENTS 9003192 4/1990 PCT Int'l Appl. ................ 422/125

Primary Examiner—Robert J. Warden
Assistant Examiner—Stephanie Blythe
Attorney, Agent, or Firm—Michael Ebert

[57] ABSTRACT

A kit for formulating and generating different mood modifying or therapeutic aromas, the kit including a battery of vials each containing a different essential fragrance oil, thereby making it possible for a user to compound a blend of oils producing an aroma having the desired effect. Also provided is a vessel formed of cermaic or other dielectric material and having a removable cover. The inner and outer surfaces of the vessel have a glaze thereon whose composition is such that when the vessel is placed in a microwave oven and subjected to microwave energy, this energy is absorbed only by the glaze, as a consequence of which the interior of the vessel is heated to an elevated temperature and acts to volatilize a charge of oil deposited in the vessel by the user, the constituents of the charge being derived from oils taken from selected vials as formulated by the user. The resultant aromatic vapor having the desired fragrance is released into the atmosphere when the heated vessel is withdrawn from the oven and its cover is taken off.

5 Claims, 2 Drawing Sheets

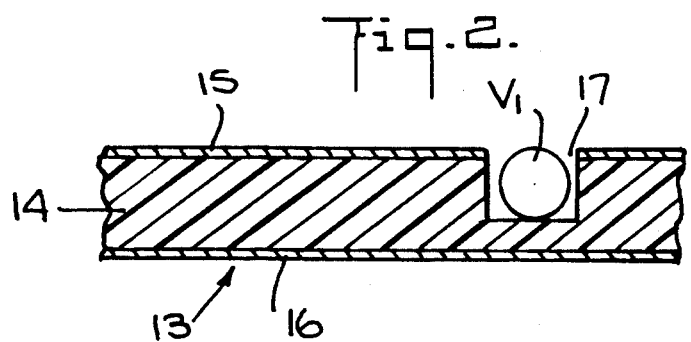
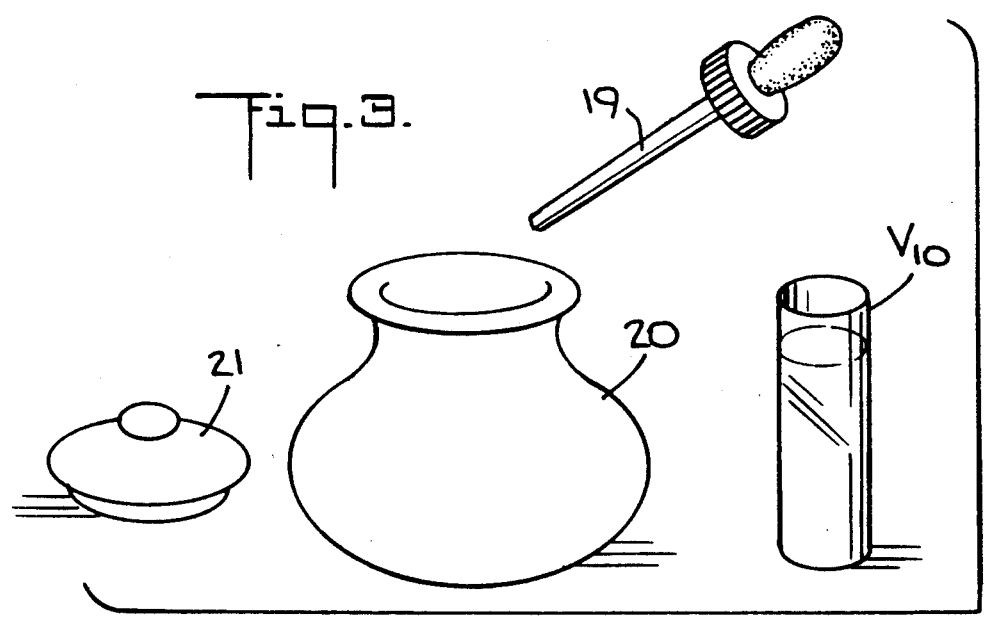
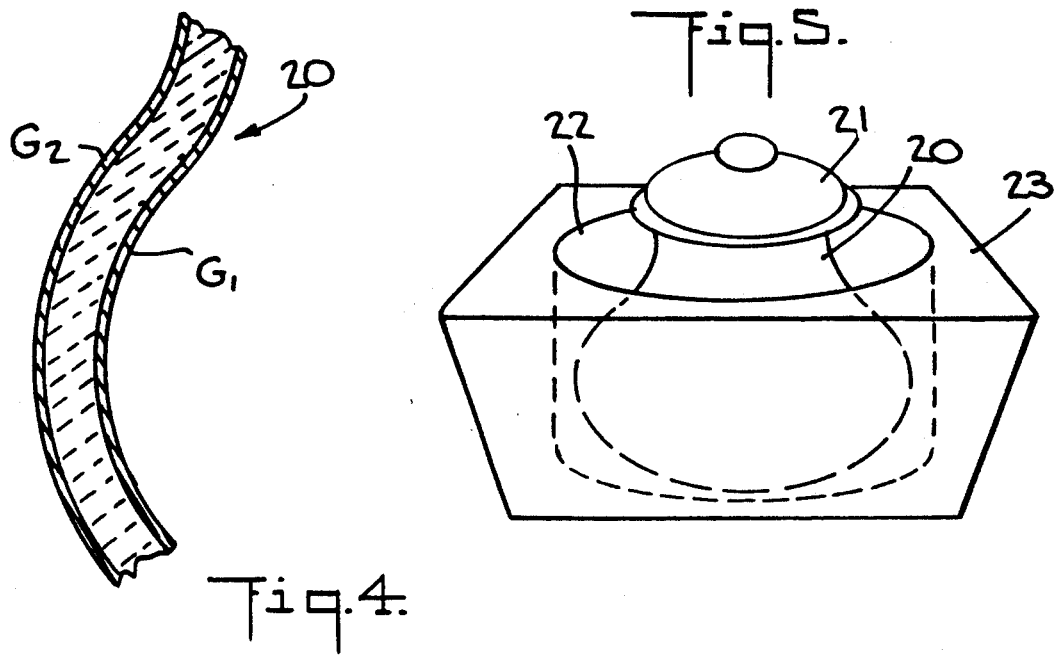

KIT FOR FORMULATING AND GENERATING DIFFERENT AROMAS

BACKGROUND OF INVENTION

1. Field of Invention

This invention relates generally to the formulation and generation of different mood-modifying or therapeutic aromas, and more particularly to a kit which makes it possible for a user to formulate a blend of oils to create an oil charge which when heated and volatilized generates an aromatic vapor having the desired effect.

2. Status of Prior Art

The field of aroma therapy is based on the recognition that fragrances have mood-altering, and, in some instances, therapeutic properties. Thus, depending on the nature of the aroma to which an individual is exposed, he may be repelled, stimulated, depressed, excited or soothed by the aroma.

The olfactory response of most individuals is such that the inhalation of the aroma of chamomile tends to induce sleep, this being preferable to the use of sleeping pills which may have adverse side effects. And the reason many spas and health centers subject individuals being treated to the aroma of eucalyptus is to relieve congestion. In experimental use in space programs are fragrances that act to stimulate astronauts during their tedious hours in space. And the use of incense to create a spiritual environment goes back to the earliest times in history. In many households, aromas are used to mask bathroom and kitchen odors and to create a more pleasing environment.

The aroma of perfumes and perfume-based products such as colognes and toilet waters was originally derived from the essential oil of plants. However, since the early 19th century, chemists have succeeded in analyzing many essential oils and in developing thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The leading producers of essential oils from which fragrances are made are the East Indies and the South of France. Turkey is noted for attar of roses, Algeria for geranium oils, Italy for citrus oils, and England for lavender and mint oils.

In my prior patent, U.S. Pat. No. 5,007,529, entitled "Microwave-Heatable Air-Freshener Package," there is disclosed an air freshener package activated by microwave energy to discharge into the atmosphere an aromatic vapor comparable to that exuded by a potpourri. The package comprises a container formed of thermal insulation material permeable to microwave energy and having a vent therein. Stored in the package is a porous pad impregnated with a liquid fragrance which simulates the aroma of a natural potpourri. When the package is irradiated in a microwave oven, the liquid fragrance is then heated to a level causing it to volatilize to generate an aromatic vapor. This vapor is discharged into the atmosphere through the vent when the package is removed from the oven and placed in a room. The temperature level is substantially maintained for a protracted period by the thermal insulation so that the aromatic vapor suffuses the room.

A natural potpourri which exudes fragrant scents is a mixture of aromatic herbs, dried flowers and spices blended with natural oils. The package disclosed in my prior patent makes use of a liquid fragrance that has been compounded to simulate the aroma of a natural potpourri. However, while the complex and pleasing fragrance emitted by a potpourri is such that it serves to mask unpleasant odors, the user of the package disclosed in my prior patent has no control over the nature of aromatic vapor that is emitted, for this is predetermined by the manufacturer of the package.

The need exists, therefore, for a microwave or otherwise activated aroma generator whose emitted aroma can be selected by the user of the generator so as to carry out a desired mood-modifying or therapeutic action.

It is to be noted that in the 18th Century in Europe, before the production of perfumes was taken over by manufacturers who both made and marketed perfumes, each rich household in Europe usually had a so-called "still room" in which the lady of the house would from a stock of essential oils formulate a perfume that suited her taste. It is rare for an acceptable perfume to make use of a single essential oil, for to be pleasing, a blend of different oils is produced in which the relative proportions of the oils are such as to produce the aroma desired. Hence those ladies who became practiced in blending essential oils, in doing so also developed special perfume recipes and these were usually closely guarded.

SUMMARY OF INVENTION

In view of the foregoing, the main object of this invention is to provide a kit for formulating and generating different mood-modifying or therapeutic aromas, the kit including a battery of vials each containing a different essential fragrance oil, thereby making it possible for a user to formulate a blend of oils capable of generating generating an aroma having the effect desired.

More particularly, an object of this invention is to provide in a kit of the above type a battery of vials in a book format in which the book not only includes an array of cells for storing the vials, but also printed recipes which instruct the user how to create a variety of different blends. But the user is not bound by these recipes, for he may develop his own blends from the available stock of oils.

Yet another object of the invention is to provide a kit of the above type having a heating vessel into which a user may deposit a charge of oil whose constituents are derived from oils taken from selected vials to produce a desired aroma, the structure of the vessel being such that when it is subjected to microwave energy in a microwave oven, the interior of the vessel is heated to an elevated temperature to volatilize the charge of oil therein.

Still another object of the invention is to provide a thermally-insulated holder adapted to accommodate the vessel, so that a user will not be burned when handling the vessel in its heated state.

Briefly stated, these objects are attained in a kit for formulating and generating different mood modifying or therapeutic aromas, the kit including a battery of vials each containing a different essential fragrance oil, thereby making it possible for a user to compound a blend of oils producing an aroma having the desired effect. Also provided is a vessel formed of ceramic or other dielectric material and having a removable cover.

The inner and outer surfaces of the vessel have a glaze thereon whose composition is such that when the vessel is placed in a microwave oven and subjected to microwave energy, this energy is absorbed only by the glaze, as a consequence of which the interior of the vessel is heated to an elevated temperature and acts to volatilize a charge of oil deposited in the vessel by the user, the constituents of the charge being derived from oils taken from selected vials as formulated by the user. The resultant aromatic vapor having the desired fragrance is released into the atmosphere when the heated vessel is withdrawn from the oven and its cover is taken off.

BRIEF DESCRIPTION OF DRAWINGS

For a better understanding of the invention as well as other objects and further features thereof, reference is made to the following detailed description to be read in conjunction with the accompanying drawings, wherein:

FIG. 2 is a section taken through the back cover of the book;

FIG. 3 shows the glazed vessel included in the kit into which drops of essential oils taken from selected vials are deposited by a dropper to produce an oil charge which is a blend of the selected oils;

FIG. 4 is a section taken through a portion of the glazed vessel; and

FIG. 5 shows the vessel nested in a holder therefor.

DESCRIPTION OF INVENTION

Figure 1:
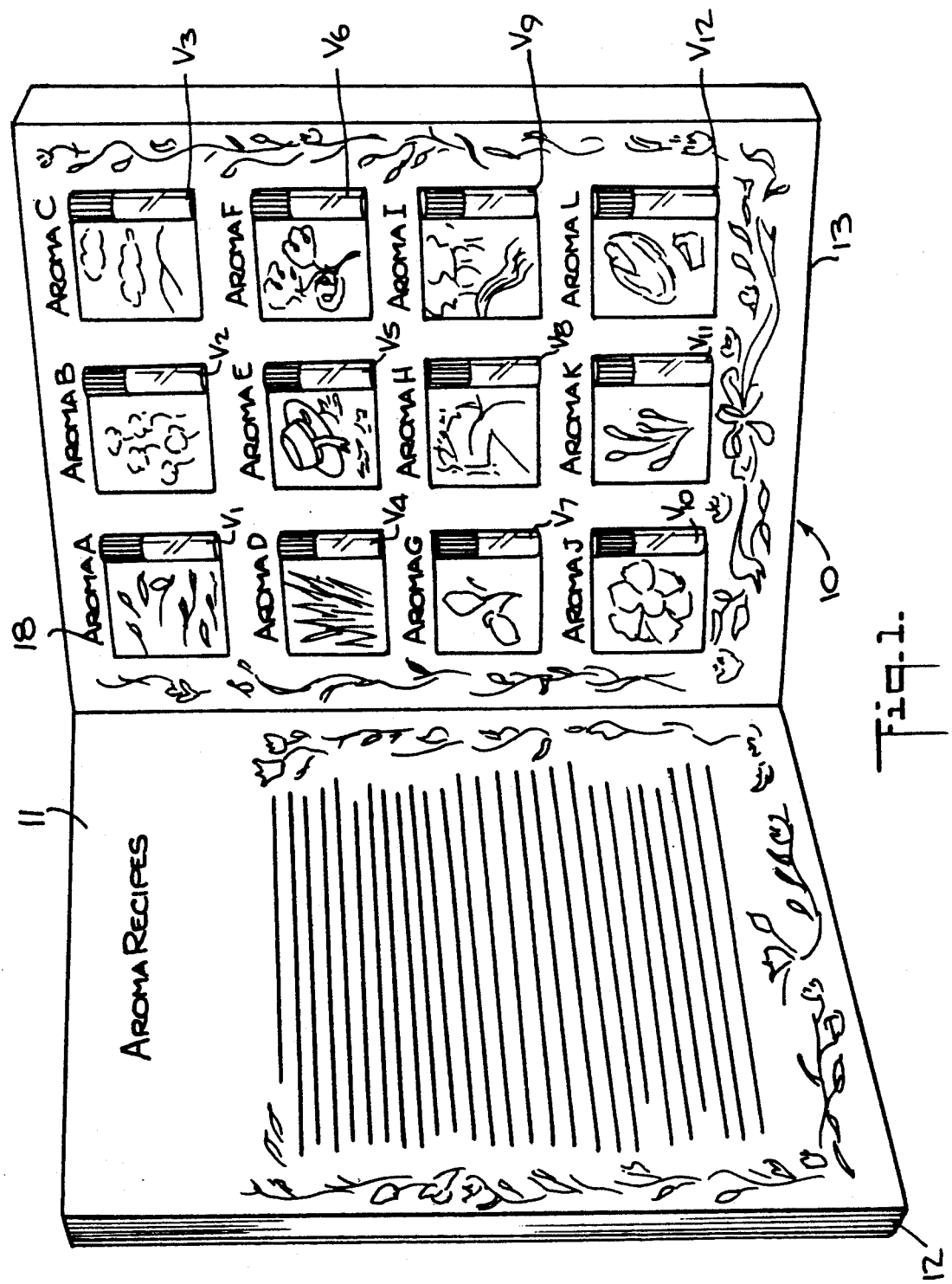
FIG. 1 is a perspective view of the book included in a kit in accordance with the invention, the book being open to expose its back cover which is composed of an array of cells for storing a battery of vials containing different essential oils.

Referring now to FIGS. 1 and 2, a kit in accordance with the invention includes a book, generally designated by numeral 10, having a set of pages 11 bound between the front and rear covers 12 and 13 of the book. Printed on pages 11 are various aroma recipes which involve blending together two or more essential oils in specified proportions to produce a potion which when activated by heat generates the desired aroma. These proportions are expressed in drops. For example, to produce, say, an aroma suggestive of a field of variegated flowers, one may then blend together two drops of aroma A, one drop of aroma D and three drops of aroma K.

The back cover, as shown in FIG. 2, is constituted by a relatively thick board having inner and outer paper plies 15 and 16 laminated thereto. The board has a rectangular array of cells 17 indented therein to accommodate twelve cylindrical glass vials $V_1$ to $V_{12}$ having removable caps, each vial containing a different essential oil for producing an aroma. Printed within a block 18 adjacent the leading edge of each cell is art work related to the particular aroma produced by the essential oil contained in this cell. Thus if the aroma is that of a lemon, the art work will illustrate lemon; if the aroma is that of roses, this flower will be illustrated. The cells are labelled Aroma A, Aroma B, Aroma C, etc., so that the recipes contained in the book can so identify the oils to be blended.

In practice, board 14 of the back cover may be formed of rigid, synthetic plastic foam material such as PVC which is molded to create the necessary cells for nesting vials $V_1$ to $V_{12}$. And instead of pages bound into the book, a separate booklet may be provided in which the recipes are printed. However, the user of the kit is not bound to use these recipes, for he is free to invent and compound his own recipe to create whatever aroma that meets his individual requirements. If, for example, the user wishes to produce a pleasing sleep-inducing aroma, he may combine a chamomile oil with an oil of roses to create a unique potion. And while book 10 houses twelve vials, in practice a greater number may be provided to afford a greater range of possibilities.

The kit, as shown in FIG. 3, also includes a standard dropper 19 constituted by a rubber bulb attached to a short glass tube. This tube is insertable into a vial to withdraw a small quantity of oil therefrom and to eject this oil from the tube as a drop into a small bowl or vessel 20 having a removable cap 21.

Vessel 20, as shown separately in FIG. 4, is formed of a dielectric material, such as clay or other ceramic whose inner and outer surfaces are glazed by glaze layers $G_1$ and $G_2$ having "lossy" electrical properties. Glazing involves the application of finely ground glass particles or glass-forming materials, or a mixture thereof, to a ceramic body and then firing this material to its melting temperature, whereby a vitreous coating is then formed on the surface of the ceramic. The resultant glaze seals the ceramic body to prevent it from absorbing moisture or liquids, and to provide an easily cleaned sanitary surface.

A glaze composition suitable for vessel 20 which is designed to be heated when exposed to microwave energy in a microwave oven is a composition which includes tin, lead, boron or other metallic or metalloid material which is not dielectric in nature and therefore imparts to the glaze "lossy" electrical properties.

In a typical microwave oven, represented in FIG. 5 by block 22, a magnetron functions to generate microwave energy at a frequency of about 100 mHz. This energy is conveyed by a wave guide to the interior of the oven to irradiate food, liquid or other substances placed therein of a nature that absorbs microwave energy. Such absorption gives rise to internal molecular friction which heats up the substance at a rate that depends on its lossy characteristics.

The ceramic from which the vessel is formed has dielectric or highly insulating electrical properties so that it is more or less permeable to microwave energy and is therefore only slightly heated thereby. And essential oils also have electrical insulating properties and are not quickly heated by microwave energy. However, the glaze, because it contains metal or metallic constituents, does not possess dielectric properties, for it is "lossy" and therefore rapidly absorbs microwave energy.

As a consequence, when a user deposits drops of oil in the vessel selected from the vials to create a desired potion, and the vessel 20 is then capped by cover 21 and placed in microwave oven 22 where it is subjected to microwave energy, this energy acts to heat the glaze coating on both the interior and exterior surfaces of the vessel. In doing so, it elevates the temperature within the interior of the vessel to a level causing the charge of oil contained in the vessel to volatilize, thereby producing an aromatic vapor which is confined within the covered vessel. In practice, cover 21 may be provided with a small vent hole to prevent an excessive rise of vapor pressure therein.

Vessel 20 is nested within a circular well 22 formed within a rectangular holder 23. Holder 23 is molded of rigid foam plastic material, such as polyurethane foam, which has dielectric properties and therefore does not absorb microwave energy. Moreover, holder 23 has thermal insulation properties so that not only is it not heated by microwave energy, but because it remains cool, it acts to thermally isolate the hand of the user from the heated vessel when the hand removes the vessel from the microwave oven. After the held vessel is removed, it is then placed at a suitable site in a room. The cover is then withdrawn from the vessel to release the aromatic vapor into the atmosphere of the room to suffuse the room with the desired aroma.

The effect of this aroma on individuals who are present in the room—that is, whether it is mood-modifying or therapeutic—depends, of course, on the nature of the potion compounded by the user.

An alternative approach to activating the potion contained in the vessel where a microwave oven is not available or where its use is not feasible, is to add boiling water to the vessel. The charge of oil contained in the vessel will float to the surface of the boiling water and be volatilized thereby to create an aromatic vapor. And because the ceramic vessel and the holder in which it is nested have thermal insulating properties, the water will be maintained for a relatively long period at an elevated temperature; and when the cover of the vessel is removed to release the vapor into the atmosphere, because the water remains very hot, volatilization will continue until all of the oil charge has been evaporated.

Thus a kit in accordance with the invention supplies a user with a stock of different essential oils which makes it possible for him to compound a potion whose aroma has the desired effect, and to activate the potion by heat to create an aromatic vapor which can be released into the atmosphere.

While there has been shown and described a preferred embodiment of a kit for formulating and generating different aromas in accordance with the invention, it will be appreciated that many changes and modifications may be made therein without, however, departing from the essential spirit thereof. Thus the holder, instead of being made of rigid foam plastic material, may be formed of wood or other material that is non-reactive to microwave energy.

I claim:

1. A kit for formulating and generating different mood-modifying aromas, said kit comprising:
    (a) a battery of vials, each containing a different essential fragrance oil, thereby making it possible for a user of the kit to compound a potion constituted by a charge of oil derived from at least one of said vials;
    (b) a vessel having a removable cover, said vessel being formed of a ceramic having dielectric properties whose inner and outer surface have a glaze coated thereon, the composition of which is electrically lossy, such that when the vessel is exposed to microwave energy in an oven, this energy is absorbed by the glaze and is heated thereby to elevate the temperature within the interior of the vessel, said glaze being formed by a mixture of vitreous particles and metallic or metalloid materials which is fired to create a lossy vitreous coating on said inner and outer surface that seals the ceramic to prevent it from absorbing oil; and
    (c) means to deposit a charge of oil in said vessel before it is exposed to microwave energy, after which the charged vessel is covered and placed in said oven and heated therein, whereby said charge is then volatilized to produce an aromatic vapor which when the vessel is withdrawn from the oven and its cover removed, is discharged into the atmosphere, wherein said battery of vials, said vessel and said means to deposit are included in a common package.

2. A kit as set forth in claim 1, wherein said vessel has a bulbous form, further including an open top holder formed of dielectric, thermally insulating material having a circular well therein to accommodate said covered vessel so that the cover thereof projects above the open top of the holder, whereby the heated vessel nested in the holder can be withdrawn by the hand of a user from the oven without injury to the hand, and the cover can then be removed to release the volatilized charge into the atmosphere.

3. A kit as set forth in claim 1, further including a board having an array of like cells indented therein to accommodate said battery of vials, said board forming the back cover of a book whose pages have printed thereon recipes for various potions, each of which is composed of at least one drop of oil taken from selected vials.

4. A kit as set forth in claim 3 wherein adjacent each cell on the face of the board is a printed illustration related to the aromatic nature of the oil contained in the vial occupying the cell.

5. A kit as set forth in claim 3, wherein said means to deposit is constituted by a dropper to extract oil from said vials and to provide drops to create said potions.

* * * * *